United States Patent
Ikenaga et al.

(10) Patent No.: US 9,826,124 B2
(45) Date of Patent: *Nov. 21, 2017

(54) IMAGE PROCESSING APPARATUS AND METHOD FOR CORRECTING COLOR COMPONENTS

(71) Applicant: Sony Corporation, Tokyo (JP)

(72) Inventors: Yuichiro Ikenaga, Kanagawa (JP); Toru Shiono, Tokyo (JP); Tetsuro Hoshino, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/049,395

(22) Filed: Feb. 22, 2016

(65) Prior Publication Data
US 2016/0173734 A1     Jun. 16, 2016

Related U.S. Application Data

(63) Continuation of application No. 14/522,814, filed on Oct. 24, 2014, now Pat. No. 9,294,656.

(30) Foreign Application Priority Data

Nov. 19, 2013     (JP) .................................. 2013-239374

(51) Int. Cl.
*H04N 1/60*     (2006.01)
*G06K 9/00*     (2006.01)
(Continued)

(52) U.S. Cl.
CPC ............ *H04N 1/603* (2013.01); *G01J 3/4406* (2013.01); *G01J 3/46* (2013.01); *G01N 21/6428* (2013.01);
(Continued)

(58) Field of Classification Search
CPC .......... H04N 1/603; G01J 3/4406; G01J 3/46; G01N 21/6428; G01N 21/6456;
(Continued)

(56) References Cited

U.S. PATENT DOCUMENTS

2008/0002037 A1     1/2008 Ueda

FOREIGN PATENT DOCUMENTS

| JP | 2004-86031 | | 3/2004 |
|---|---|---|---|
| JP | 2004235851 | A * | 8/2004 |
| JP | 2010-98719 | | 4/2010 |

* cited by examiner

*Primary Examiner* — Amandeep Saini
(74) *Attorney, Agent, or Firm* — Oblon, McClelland, Maier & Neustadt, L.L.P.

(57) ABSTRACT

An image processing apparatus includes: an interface unit configured to input an image signal from an imaging apparatus that exposes a specimen dyed with a fluorescent dye to excitation light and images fluorescence by a color imaging element; and a color correction circuit configured to retain information on a percentage of each of a component of a second color and a component of a third color with respect to a component of a first color corresponding to the excitation light in the image signal, which is determined in advance based on color filter spectral characteristics of the color imaging element, and reduce each of an amount corresponding to the percentage of the component of the second color and an amount corresponding to the percentage of the component of the third color from the input image signal.

18 Claims, 9 Drawing Sheets

(51) Int. Cl.
*G01N 21/64* (2006.01)
*G01J 3/44* (2006.01)
*G01J 3/46* (2006.01)
*G02B 21/36* (2006.01)

(52) U.S. Cl.
CPC ..... G01N 21/6456 (2013.01); G01N 21/6458 (2013.01); G02B 21/365 (2013.01); G06K 9/00127 (2013.01); *G01N 2021/6417* (2013.01); *G01N 2021/6439* (2013.01); *G01N 2201/121* (2013.01)

(58) Field of Classification Search
CPC ....... G01N 21/6458; G01N 2021/6417; G01N 2021/6439; G06K 9/00127
USPC .......................................................... 382/133
See application file for complete search history.

$$\begin{pmatrix} \text{Rout} \\ \text{Gout} \\ \text{Bout} \end{pmatrix} = \begin{pmatrix} RR & RG & RB \\ GR & GG & GB \\ BR & BG & BB \end{pmatrix} \begin{pmatrix} \text{Bin}*\text{Nr\%} \\ \text{Bin}*\text{Ng\%} \\ \text{Bin} \end{pmatrix}$$

$$\begin{pmatrix} 2.48 \\ 1.36 \\ 2.48 \end{pmatrix} = \begin{pmatrix} 1.55 & -0.24 & -0.31 \\ -0.03 & 1.67 & -0.64 \\ 1.55 & -0.24 & -0.31 \end{pmatrix} \begin{pmatrix} 18 \\ 25 \\ 62.25 \end{pmatrix}$$

FIG.9A $$\begin{pmatrix} 2.48 \\ 13.86 \\ 13.54 \end{pmatrix} = \begin{pmatrix} 1.55 & -0.24 & -0.31 \\ 0.59 & 0.59 & -0.19 \\ 1.30 & -0.24 & -0.06 \end{pmatrix} \begin{pmatrix} 18 \\ 25 \\ 62.25 \end{pmatrix}$$

FIG.9B $$\begin{pmatrix} 13.54 \\ 17.35 \\ 13.54 \end{pmatrix} = \begin{pmatrix} 1.30 & -0.24 & -0.06 \\ 0.59 & 0.50 & -0.09 \\ 1.30 & -0.24 & -0.06 \end{pmatrix} \begin{pmatrix} 18 \\ 25 \\ 62.25 \end{pmatrix}$$

FIG.9C

IMAGE PROCESSING APPARATUS AND METHOD FOR CORRECTING COLOR COMPONENTS

CROSS REFERENCE TO RELATED APPLICATIONS

This application is a continuation of U.S. application Ser. No. 14/522,814 filed Oct. 24, 2014, which claims the benefit of Japanese Priority Patent Application JP 2013-239374 filed Nov. 19, 2013, the entire contents of both of which are incorporated herein by reference.

BACKGROUND

The present technology relates to an image processing apparatus that processes a fluorescence image captured by an imaging apparatus and to an image processing method.

Image processing apparatuses each of which captures an observation image of a fluorescence microscope by an imaging element and acquires it as electronic image data are used in the fields of, for example, medical science, biological studies, and examinations.

The observation image of the fluorescence microscope is an image of weak fluorescence. It is thus difficult to obtain a contrast (visual difference) between an image of a cell portion dyed with the fluorescence and an image of a background portion without the cell.

In this context, Japanese Patent Application Laid-open No. 2004-086031 describes a technique of black balance correction of increasing the contrast between the image of the cell portion and the image of the background portion by subtracting, from the observation image, a luminance of the background portion manually specified by a user such that the background portion is darkened.

In addition, Japanese Patent Application Laid-open No. 2010-098719 discloses a technique for automatically performing white balance correction or black balance correction without the user manually specifying the background portion.

SUMMARY

In the field of the image processing apparatus that processes a fluorescence image obtained by an imaging apparatus such as a fluorescence microscope and generates an image for observation, a technique for generating a fluorescence image easily observable by the user is becoming more and more important and needs to be developed.

In view of the above-mentioned circumstances, it is desirable to provide an image processing apparatus capable of generating a fluorescence image easily observable by the user and an image processing method.

According to an embodiment of the present technology, there is provided an image processing apparatus including:

an interface unit configured to input an image signal from an imaging apparatus that exposes a specimen dyed with a fluorescent dye to excitation light and images fluorescence by a color imaging element; and a color correction circuit configured to retain information on a percentage of each of a component of a second color and a component of a third color with respect to a component of a first color corresponding to the excitation light in the image signal, which is determined in advance based on color filter spectral characteristics of the color imaging element, and reduce each of an amount corresponding to the percentage of the component of the second color and an amount corresponding to the percentage of the component of the third color from the input image signal.

The color correction circuit may be configured to reduce the component of the first color from the input image signal.

The color correction circuit may be a linear matrix transformation circuit.

The image processing apparatus according to the present technology may further include a white balance adjustment circuit configured to reduce either one of the component of the second color and the component of the third color from the input image signal at a preceding stage of the color correction circuit.

The fluorescent dye may be fluorescein.

According to another embodiment of the present technology, there is provided an image processing method including:

determining, based on color filter spectral characteristics of a color imaging element that exposes a specimen dyed with a fluorescent dye to excitation light and images fluorescence, a percentage of each of a component of a second color and a component of a third color with respect to a component of a first color corresponding to the excitation light in an image signal of the color imaging element; and reducing each of an amount corresponding to the percentage of the component of the second color and an amount corresponding to the percentage of the component of the third color from the image signal input from the color imaging element.

As described above, according to embodiments of the present technology, it is possible to generate a fluorescence image easily observable by the user.

These and other objects, features and advantages of the present disclosure will become more apparent in light of the following detailed description of best mode embodiments thereof, as illustrated in the accompanying drawings.

BRIEF DESCRIPTION OF DRAWINGS

FIG. 9A is a view showing a setting example of a linear matrix transformation coefficient;

FIG. 9B is a view showing another setting example of the linear matrix transformation coefficient; and FIG. 9C is a view showing still another setting example of the linear matrix transformation coefficient.

DETAILED DESCRIPTION OF EMBODIMENTS

Hereinafter, an embodiment of the present technology will be described with reference to the drawings.

First Embodiment

Figure 1:
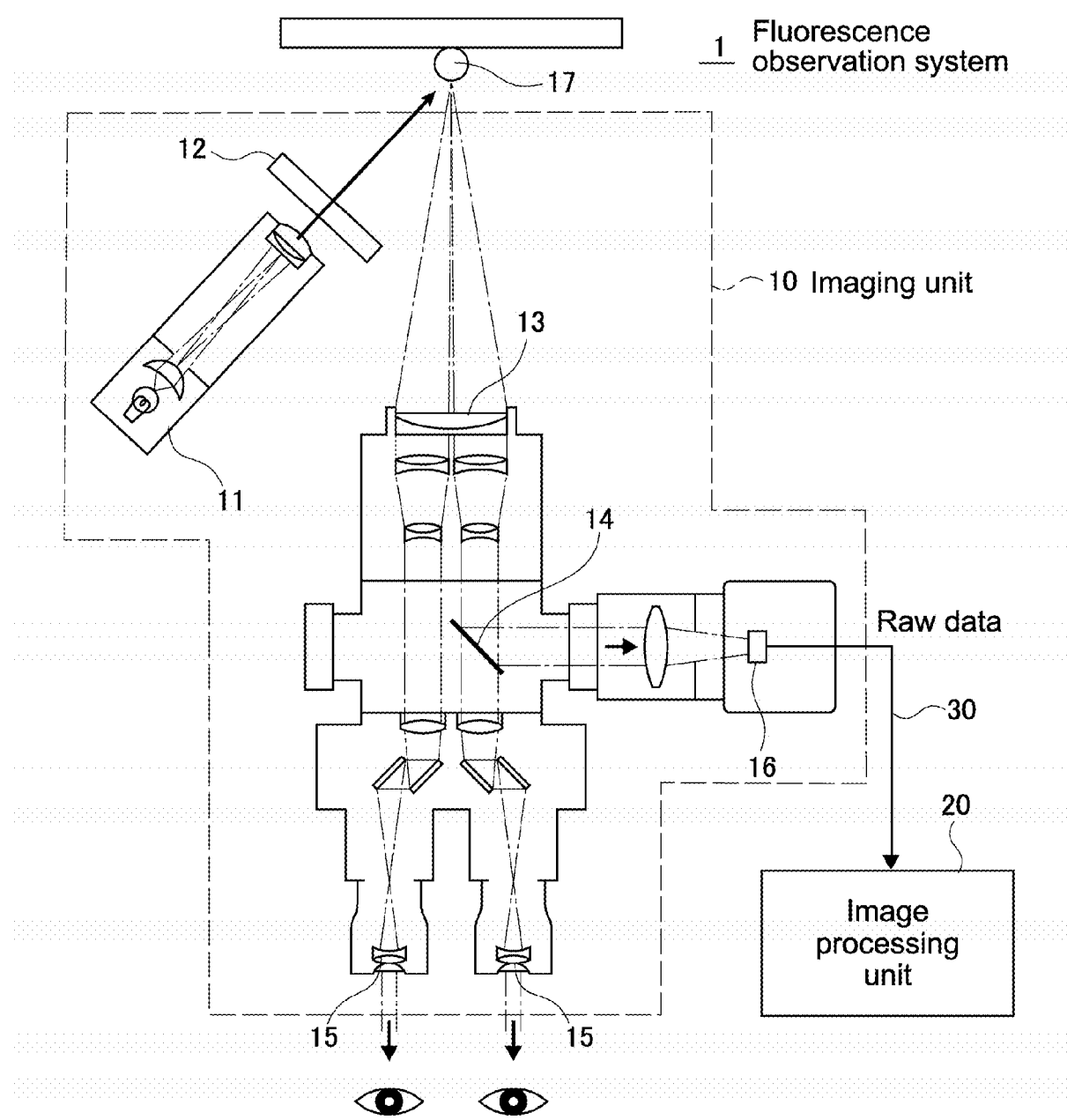
FIG. 1 is a view showing a configuration of a fluorescence observation system 1 according to a first embodiment of the present technology.

FIG. 1 is a view showing a configuration of a fluorescence observation system 1 according to a first embodiment of the present technology.

This fluorescence observation system 1 includes an imaging unit 10 and an image processing unit 20. The imaging unit 10 and the image processing unit 20 are connected to each other through an image transmission channel 30.

[Imaging Unit 10]

The imaging unit 10 includes a light source 11, an excitation filter 12, an objective lens 13, a beam splitter 14, an eye piece 15, a CMOS image sensor 16, and the like.

The light source 11 is a halogen lump, a xenon arc lamp, or the like and emits white light including the wavelength band of visible light.

The excitation filter 12 is an optical filter that causes light having a wavelength for exciting a fluorescent material of a specimen 17 to pass therethrough. The light (excited light) passing through the excitation filter 12 irradiates the specimen 17.

Figure 2:
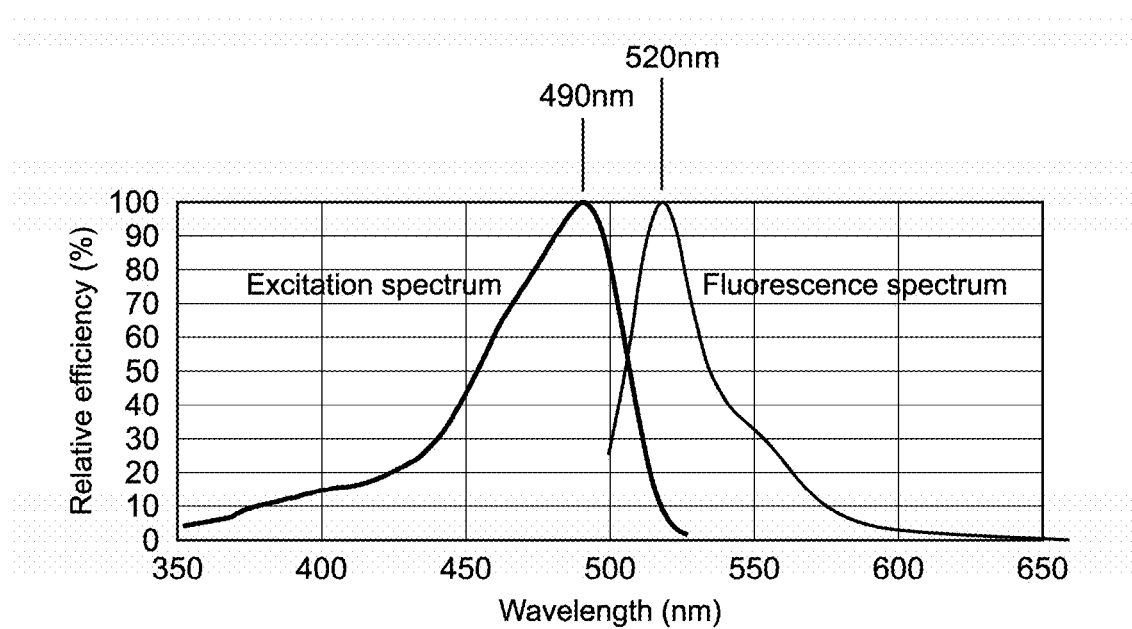
FIG. 2 is a view showing fluorescence characteristics of fluorescein.

The specimen 17 is a biological tissue slice, a cell group, or the like dyed with the fluorescent dye. Here, a case where the fluorescein is used as the fluorescent dye is assumed. As shown in FIG. 2, the fluorescein is fluorescent dye that emits green light having a center wavelength of 520 nm when exposed to blue light having a center wavelength of 490 nm.

Figure 3:
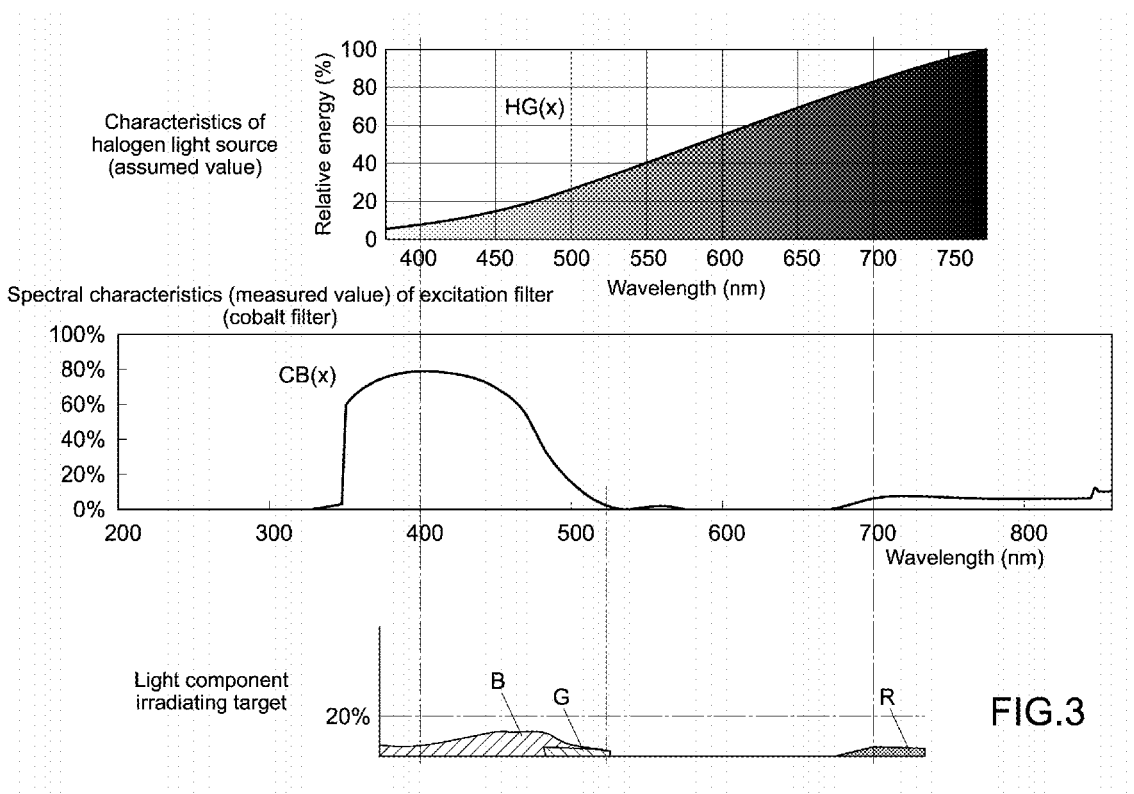
FIG. 3 is a view showing spectral characteristics of a cobalt filter and light components that passes through the cobalt filter and irradiates the specimen 17.

FIG. 3 is a view showing spectral characteristics of a cobalt filter that causes mainly light in a wavelength region of blue (B) to pass therethrough as the excitation filter 12 and light components that passes through the cobalt filter and irradiates the specimen 17. As can be seen from the figure, the cobalt filter is an optical filter that causes light in a B-wavelength region of from about 350 nm to about 510 nm. Here, B corresponds to a "first color" in the scope of claims. G and R correspond to a "second color" and a "third color" in the scope of claims.

Light emitted from the specimen 17 enters the objective lens 13. The beam splitter 14 is provided in a light path between the objective lens 13 and the eye piece 15. That is, light from the objective lens 13 is distributed into light directed to the eye piece 15 and light directed to the CMOS image sensor 16. With this, the same image as an observation image that an observer views through the eye piece 15 can be captured.

Note that, although shown in the figure, an IR cut filter is provided at a preceding stage of the CMOS image sensor 16. The IR cut filter is an optical filter for removing wavelength components equal to or larger than 680 nm, for example, that is a wavelength region of red (R).

A complementary MOS (CMOS) image sensor 16 receives light passing through the IR cut filter for each of R, G, and B selected by an optical filter to generate an electrical signal and digitalizes it to generate Raw data. The generated Raw data is transmitted to the image processing unit 20 through the image transmission channel 30.

[Color Mixing in Fluorescence and Color Components of Background]

Next, color mixing in fluorescence, which is caused when the imaging unit 10 captures a fluorescence image, and color components of the background.

Figure 4:
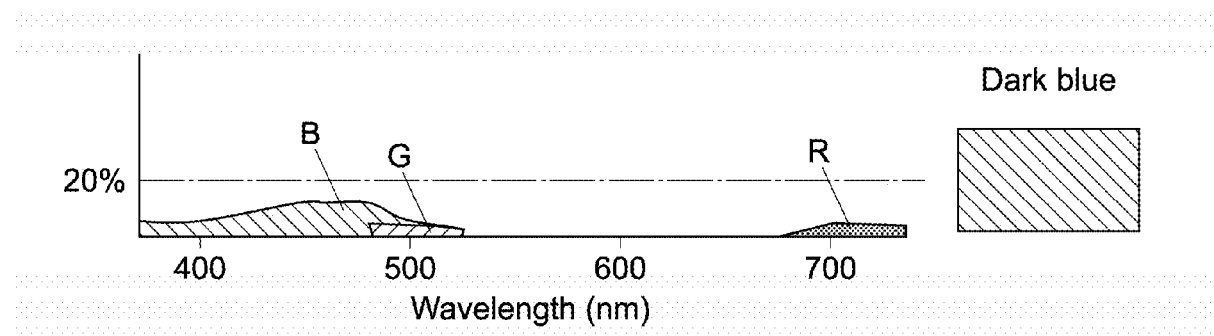
FIG. 4 is a view showing light components emitted from the specimen 17 when the specimen 17 not dyed with fluorescein is irradiated with light in a B-wavelength region of from about 350 nm to about 510 nm.

FIG. 4 is a view showing light components emitted from the specimen 17 when light in the B-wavelength region of from about 350 nm to about 510 nm limited by the excitation filter 12 irradiates the specimen 17 not dyed with fluorescein. At this time, light emitted from the specimen 17 is mainly reflected light. Components of the reflected light is equal to components of the light (FIG. 3) irradiating the specimen 17. The color of an image captured at this time is dark blue color.

Figure 5:
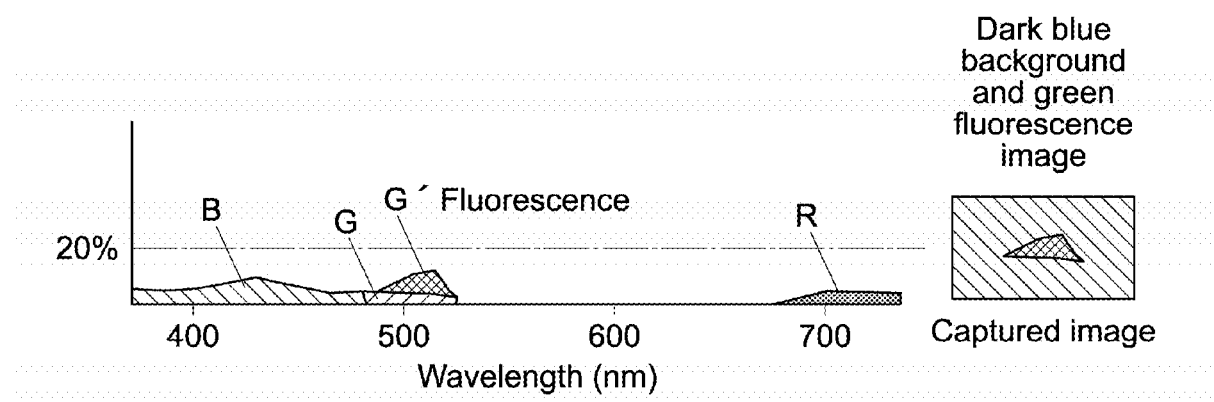
FIG. 5 is a view showing light components emitted from the specimen 17 when the specimen 17 dyed with fluorescein is irradiated with the light in the B-wavelength region of from about 350 nm to about 510 nm.

FIG. 5 is a view showing light components emitted from the specimen 17 when light in the B-wavelength region of from about 350 nm to about 510 nm irradiates the specimen 17 dyed with the fluorescein. In this case, by the specimen 17 died with the fluorescein being exposed to the light in the B-wavelength region, the fluorescence is generated. In FIG. 5, G' indicates G-color components of the fluorescence.

Figure 6:
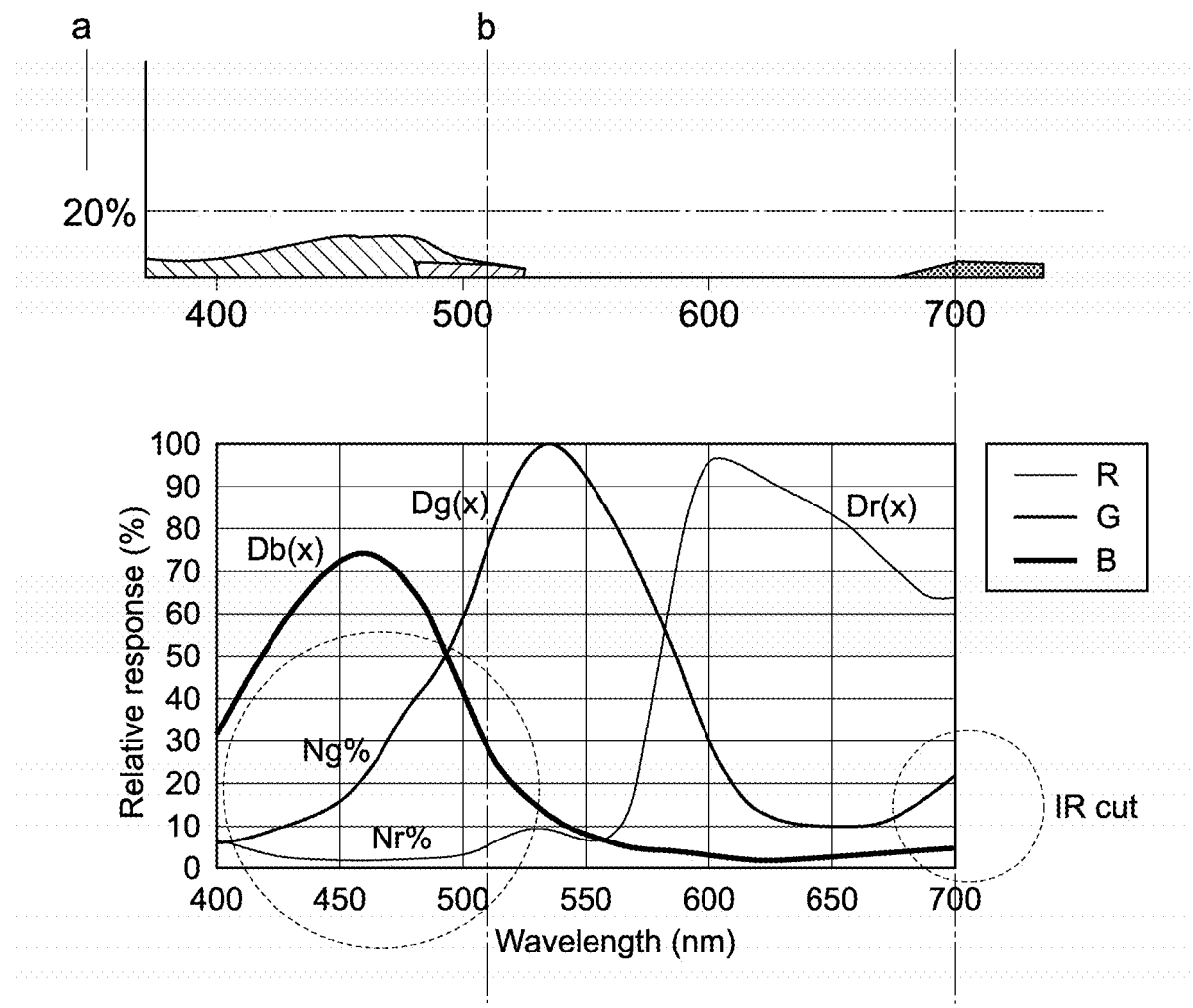
FIG. 6 is a view showing color filter spectral characteristics of a CMOS image sensor 16.

FIG. 6 is a view showing color filter spectral characteristics of the CMOS image sensor 16.

As can be seen from the color filter spectral characteristics, G and R-pixels of the CMOS image sensor 16 react also to the light in the B-wavelength region of from about 350 nm to about 510 nm that is a transmission region of the cobalt filter. Thus, a signal detected by the CMOS image sensor 16 is the components of the fluorescence to which components (mixed components) generated when R, G, and B-pixels react to the reflected light in the B-wavelength region of from about 350 nm to about 510 nm.

In this manner, the CMOS image sensor 16 outputs a sum of G-components generated by reacting to the fluorescence and R, G, and B-components generated by reacting to the reflected light in the B-wavelength region of from 350 nm to about 510 nm. Thus, it is not possible to obtain the true color of the fluorescence image and obtain a sufficient color contrast between a background portion and the fluorescence image because the background portion is dark blue. The present technology has been made for at least improving this point.

Hereinafter, details thereof will be described.

With respect to the light in a G-wavelength region of from about 350 nm to about 510 nm, the R, G, and B-components detected by the CMOS image sensor 16 are expressed as follows.

[Formula 1]

$$R = \int_a^b \{E^* HG(x)^* CB(x)^* Dr(x)\} \quad (1)$$

$$G = \int_a^b \{E^* HG(x)^* CB(x)^* Dg(x)\} \quad (2)$$

$$B = \int_a^b \{E^* HG(x)^* CB(x)^* Db(x)\} \quad (3)$$

Where E denotes energy (constant) of the light source 11, HG(x) denotes characteristics (spectral distribution) indicative of energy distribution state of the light source 11, CB(x) denotes the spectral characteristics of the cobalt filter, Db(x), Dg(x), and Dr(x) denote B, G, and R-color filter spectral characteristics of the CMOS image sensor 16, respectively, and a and b denote the transmission region of the cobalt filter (G-wavelength region of from about 350 nm to about 510 nm).

Ng % is a percentage of components detected by the G-pixels of the CMOS image sensor 16 with respect to components detected by the B-pixels in the G-wavelength region of from about 350 nm to about 510 nm. That is, it is expressed by Ng %=G/B.

Nr % is a percentage of components detected by the R-pixels of the CMOS image sensor 16 with respect to the components detected by the B-pixels in the wavelength region limited by the cobalt filter. That is, it is expressed by Nr %=R/B.

As described above, components detected by the CMOS image sensor 16 when the specimen 17 dyed with the fluorescein is irradiated with the light in the G-wavelength region of from about 350 nm to about 510 nm are a sum of the G-components generated by reacting to the fluorescence and the R, G, and B-components generated by reacting to the reflected light in the B-wavelength region of from 350 nm to about 510 nm.

Figure 7:
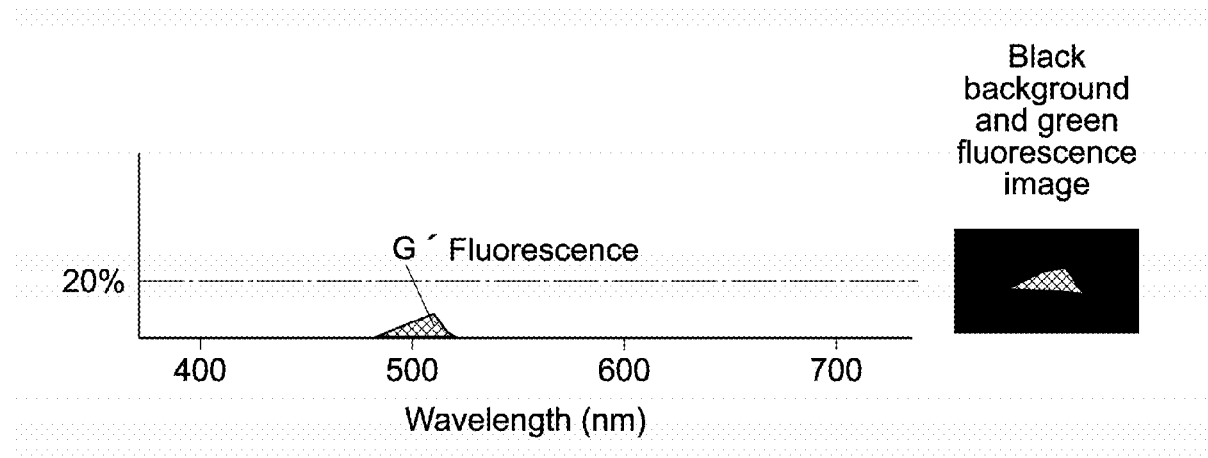
FIG. 7 is a view showing a correction result of color components.

Thus, if G=B*Ng %, R=B*Nr %, and the B-components are removed from the all R, G, and B-components detected by the CMOS image sensor, only color components G' of G generated by reacting to the fluorescence remain as shown in FIG. 7.

By adjusting the color components as described above, the true G-color of the fluorescence image can be obtained. Further, the background portion is closer to the true black because the color components are removed, and the color contrast between the background and the fluorescence portion is improved.

Next, a circuit that adjusts the above-mentioned color components from the output of the CMOS image sensor 16 will be described.

[Configuration of Image Processing Unit 20]

Figure 8:
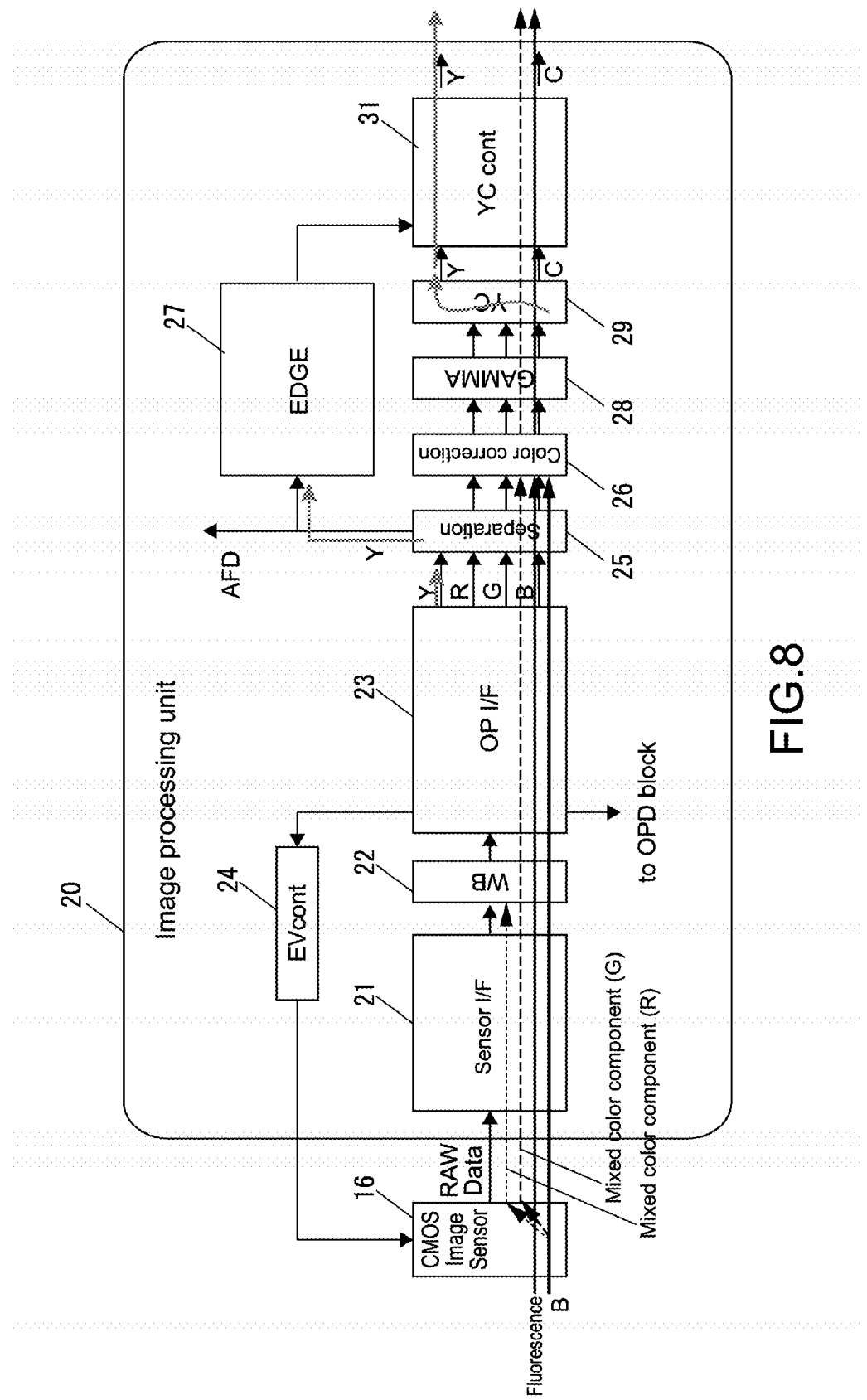
FIG. 8 is a view showing a configuration of the image processing unit 20 shown in FIG. 1.

FIG. 8 is a view showing a configuration of the image processing unit 20.

The Raw data that is the output of the CMOS image sensor 16 is input in the image processing unit 20 through a sensor I/F 21.

The Raw data input through the sensor I/F 21 is introduced into a white balance adjustment circuit 22.

The white balance of the image is adjusted at the white balance adjustment circuit 22. An optical interface circuit (OP I/F) 23 supplies the output of the white balance adjustment circuit 22 to an EV correction circuit 24. The OP I/F 23 interpolates the color, generates the R, G, and B-color signals, and further generates a luminance signal (Y) for edge processing from the G-signal, for example. The OP I/F 23 introduces the R, G, and B-color signals and the luminance signal (Y) into a separation circuit 25. The EV correction circuit 24 is a circuit that adjusts the exposure of the CMOS image sensor 16 for adjusting the brightness of the image.

The separation circuit 25 introduces the R, G, and B-color signals into a color correction circuit 26 and introduces the luminance signal (Y) into an edge processing circuit 27. At the edge processing circuit 27, edge(s) is detected from the luminance signal (Y), components of the detected edge are adjusted, and so on.

The color correction circuit 26 is a circuit that adjusts the above-mentioned R, G, and B-color components by linear matrix transformation. In the linear matrix transformation, the color components are adjusted by matrix operation on the R, G, and B-color signals.

The output of the color correction circuit 26 is introduced into a gamma correction circuit 28, subjected to gamma correction there, and converted by a YC conversion circuit 29 into the luminance signal (Y) and a color difference signal (C). The luminance signal (Y) is added to the edge components introduced from the edge processing circuit 27 and becomes the luminance signal (Y) in which the edge is emphasized. The edge-emphasized luminance signal (Y) is subjected to a process such as noise removal by a YC processing circuit 31 and output. On the other hand, the color difference signal (C) is also subjected to a process such as noise removal by the YC processing circuit 31 and output.

Note that the image processing unit 20 is specifically constituted of one large scale integration (LSI) or a plurality of LSIs, ICs, and the like.

[Color Adjustment of Linear Matrix Transformation]

A matrix operation formula used in the linear matrix transformation is shown.

[Formula 2]

$$\begin{pmatrix} Rout \\ Gout \\ Bout \end{pmatrix} = \begin{pmatrix} RR & RG & RB \\ GR & GG & GB \\ BR & BG & BB \end{pmatrix} \begin{pmatrix} Rin \\ Gin \\ Bin \end{pmatrix} \quad (4)$$

Here, out of coefficients RR, RG, RB, GR, GG, GB, BR, BG, and BB of nine elements in the matrix, RR, GG, and BB are automatically calculated such that a sum of values of three coefficient in a row to which each of them belongs is "1". Thus, the coefficients that should be actually selected are the following six: RG, RB, GR, GB, BR, and BG.

In order to select the above-mentioned six coefficients, values of R=B*Nr %, G=B*Ng %, and the B-components derived from color filter spectral characteristics of the CMOS image sensor 16 are used as an input. At this time, the above-mentioned coefficients are selected such that the output of each of R, G, and B is closer to "0." That is, the coefficients are selected such that the following formula is satisfied.

[Formula 3]

$$\begin{pmatrix} Rout \\ Gout \\ Bout \end{pmatrix} \begin{pmatrix} (1-RG-RB) & RG & RB \\ GR & (1-GR-GB) & GB \\ BR & BG & (1-BR-BG) \end{pmatrix} \quad (5)$$

$$\begin{pmatrix} Bin * Nr\% \\ Bin * Ng\% \\ Bin \end{pmatrix} \approx \begin{pmatrix} 0 \\ 0 \\ 0 \end{pmatrix}$$

In actual operation, the color correction circuit 26 in which the coefficients are selected in the above-mentioned manner is used to perform the color adjustment with respect to each of the input R, G, and B-components.

[Specific Coefficient Setting Examples]

FIGS. 9A, 9B, and 9C show specific coefficient setting examples.

FIG. 9A shows a setting example in which the output of each of R, G, and B was closest to "0" among the three setting examples, that is, a theoretically optimal setting example. The effect of the suppression of color mixing and improvement of the contrast was as expected. However, in a low-luminance environment or with a large negative coefficient value, the noise amount can be increased.

FIG. 9B is a setting example in which the coefficient values of GR, GG, GB, BR, and BB were changed for reducing the noise. In this setting, the negative coefficient value was decreased, and hence the effect of the suppression of color mixing and improvement of the contrast was slightly reduced but the effect of reduction of the noise amount has been recognized.

FIG. 9C is a setting example in which the coefficients of RR, RB, GG, and GB were further changed from the setting example shown in FIG. 9B. In this setting, the negative coefficient value was further decreased, and hence the effect of the suppression of color mixing and improvement of the contrast was further reduced but a sufficient effect of reduction of the noise amount has been recognized.

Note that, in accordance with the relationship among RR+RG+RB=1, GR+GG+GB=1, and BR+BG+BB=1, if one coefficient in each row of the matrix is determined, another coefficient is also determined according to the following formulae (6), (7), and (8).

$$(1-RG-RB)*Nr\% + RG*Ng\% + RB = 0$$

$$Nr\% + (Ng\% - Nr\%)*RG + (1-Nr\%)*RB = 0$$

$$RG = -((1-Nr\%)*RB - Nr\%)/(Ng\% - Nr\%) \quad (6)$$

$$Nr\%*GR + Ng\% - Ng\%*GR - Ng\%*GB + GB = 0$$

$$(Nr\% - Ng\%)*GR + (1-Ng\%)*GB + Ng\% = 0$$

$$GR = ((Ng\% - 1)*GB - Ng\%)/(Nr\% - Ng\%) \quad (7)$$

$$Nr\%*BR + Ng\%*BG + 1 - BR - BG) = 0$$

$$(Nr\% - 1)*BR + (Ng\% - 1)*BG + 1 = 0$$

$$BR = (-1 - (Ng\% - 1)*BG)/(Nr\% - 1) \quad (8)$$

Although the case where the constraints of RR+RG+RB=1, GR+GG+GB=1, and BR+BG+BB=1 are present has been described in the above, the present technology is not limited thereto. If these constraints are not present, it is possible to select the coefficient values with a higher degrees of freedom.

[Reduction of R-Components at White Balance Adjustment Circuit]

Although the above-mentioned color correction is performed only by the linear matrix transformation at the color correction circuit 26, the color correction may be performed partially at the white balance adjustment circuit.

For example, the R-components may be reduced as much as possible at the white balance adjustment circuit 22. In this case, the load on the coefficients set in the color correction circuit 26 can be reduced, and hence an effect of reducing the noise is provided. In other words, the calculated amount of noise is increased if the coefficients take negative large values in the linear matrix transformation. By setting a signal from which the R-components are removed at the white balance adjustment circuit 22 as a target of the linear matrix transformation, it is possible to prevent the coefficients form taking the negative large values and to reduce the amount of noise.

As described above, in the image processing unit 20 according to this embodiment, by the color correction circuit 26 or the like adjusting the R, G, and B-color components, the components (mixed color components) generated when the R, G, and B-pixels of the CMOS image sensor 16 react to the reflected light in the B-wavelength region that is used as the excitation light are removed. With this, the true G-color of the fluorescence image can be obtained. The background portion is closer to the true black because the color components are removed, and the color contrast between the background and the fluorescence portion is improved.

Further, the mixed color components can be removed by the process of the color correction circuit 26 or the like within the image processing unit 20 in the above-mentioned manner, and hence it becomes unnecessary to place an absorption filter for cutting the reflected light in the B-wavelength region in the imaging unit 10. The absorption filter in the imaging unit 10 becomes unnecessary, and hence it is possible to reduce the size, weight, and cost of the imaging unit 10. In addition, an effect that the current imaging apparatus (slit lamp) can be used as it is can be also provided.

Modified Example 1

In each of the above-mentioned embodiments, the case where the fluorescein as the fluorescent dye is used is assumed. However, the present technology is applicable also to the case where other fluorescent dye is employed.

Modified Example 2

In each of the above-mentioned embodiments, by the linear matrix transformation at the color correction circuit 26, G=B*Ng %, R=B*Nr %, and the B-components are removed from the all R, G, and B-components detected by the CMOS image sensor 16.

As a modification thereof, by the linear matrix transformation at the color correction circuit 26, only G=B*Ng % and R=B*Nr % are removed from the all R, G, and B-components detected by the CMOS image sensor 16. Regarding the B-components, a circuit for removing the B-components may be provided at a subsequent stage of the color correction circuit 26 and the B-components may be removed there.

Note that the present technology may also take the following configurations.

(1) An image processing apparatus, including:
an interface unit configured to input an image signal from an imaging apparatus that exposes a specimen dyed with a fluorescent dye to excitation light and images fluorescence by a color imaging element; and
a color correction circuit configured to retain information on a percentage of each of a component of a second color and a component of a third color with respect to a component of a first color corresponding to the excitation light in the image signal, which is determined in advance based on color filter spectral characteristics of the color imaging element, and reduce each of an amount corresponding to the percentage of the component of the second color and an amount corresponding to the percentage of the component of the third color from the input image signal.

(2) The image processing apparatus according to (1), in which
the color correction circuit is configured to reduce the component of the first color from the input image signal.

(3) The image processing apparatus according to (1) or (2), in which
the color correction circuit is a linear matrix transformation circuit.

(4) The image processing apparatus according to any one of (1) to (3), further including
a white balance adjustment circuit configured to reduce either one of the component of the second color and the component of the third color from the input image signal at a preceding stage of the color correction circuit.

(5) The image processing apparatus according to any one of (1) to (4), in which
the fluorescent dye is fluorescein.

It should be understood by those skilled in the art that various modifications, combinations, sub-combinations and alterations may occur depending on design requirements and other factors insofar as they are within the scope of the appended claims or the equivalents thereof.

What is claimed is:

1. An image processing apparatus, comprising:
   at least one imaging circuit that generates an image signal from an excitation light to which an object is exposed, the image signal including color components including at least first, second and third color components;
   a memory that stores color matrix information for correcting the color components of the image signal, the color matrix information corresponding to the excitation light from which the at least one imaging circuit generates the image signal, the matrix information being determined in advance based on spectral characteristics of the at least one imaging circuit; and
   circuitry that corrects color components of the image signal based on an amount of the first color component and the color matrix information.

2. The image processing apparatus according to claim 1, wherein the at least one imaging circuit is a complementary metal-oxide-semiconductor (CMOS) imaging circuit.

3. The image processing apparatus according to claim 2, wherein the CMOS imaging circuit generates electrical signals corresponding to red, green and blue components and outputs the image signal as RAW data.

4. The image processing apparatus according to claim 1, wherein the at least one imaging circuit includes an IR cut filter.

5. The image processing apparatus according to claim 1, wherein the circuitry reduces the first color component from the input image signal.

6. The image processing apparatus according to claim 1, wherein the object is dyed with fluorescein.

7. The image processing apparatus according to claim 1, wherein a wavelength of the excitation light is between 350 nm to 510 nm.

8. The image processing apparatus according to claim 6, wherein the object includes biological tissue or cells.

9. The image processing apparatus according to claim 1, wherein the first color component is blue.

10. The image processing apparatus according to claim 1, wherein the circuitry further adjusts a white balance of the image signal from the at least one imaging circuit.

11. The image processing apparatus according to claim 1, wherein the circuitry further performs gamma correction on the image signal.

12. The image processing apparatus according to claim 1, wherein the circuitry further performs edge detection on the image signal and adjusts edge components of the image signal based on the edge detection.

13. The image processing apparatus according to claim 1, wherein the matrix information is further determined in advance based on spectral characteristics of the excitation light.

14. An imaging device comprising:
   a memory that stores color matrix information for correcting color components included in an image signal, the color matrix information corresponding to excitation light from which the image signal is generated, the matrix information being determined in advance based on spectral characteristics of at least one imaging circuit used to generate the image signal, the color components including at least first, second and third color components; and
   circuitry that corrects the color components of the image signal based on an amount of the first color component and the color matrix information.

15. The imaging device according to claim 13, comprising an imaging unit that includes a light source and the at least one imaging circuit that generates the image signal from the excitation light to which an object is exposed.

16. The imaging device according to claim 14, wherein the imaging device is a microscope.

17. The imaging device according to claim 14, wherein the light source generates white light and excitation light.

18. An image processing apparatus, comprising:
   an interface to an imaging apparatus that inputs an image signal from the imaging apparatus that exposes a specimen dyed with a fluorescent dye to excitation light and images fluorescence via at least one imaging circuit; and
   circuitry that
      retains information for correcting color components of the image signal, the color components including first, second and third color components corresponding to the excitation light from which the image signal is generated, the information being determined in advance based on color filter spectral characteristics of the at least one imaging circuit, and
      reduces each of an amount corresponding to the percentage of the second color component and an amount corresponding to the third color component from the input image signal.

* * * * *